United States Patent
Cheng et al.

(10) Patent No.: US 12,336,734 B2
(45) Date of Patent: Jun. 24, 2025

(54) VAGINAL DILATOR

(71) Applicant: Chi Mei Medical Center, Tainan (TW)

(72) Inventors: Wei-Lun Cheng, Tainan (TW);
Ing-Luen Shyu, Tainan (TW);
Chun-Pei Chiu, Tainan (TW)

(73) Assignee: CHI MEI MEDICAL CENTER, Tainan (TW)

( * ) Notice: Subject to any disclaimer, the term of this patent is extended or adjusted under 35 U.S.C. 154(b) by 415 days.

(21) Appl. No.: 18/075,356

(22) Filed: Dec. 5, 2022

(65) Prior Publication Data

US 2023/0380867 A1 Nov. 30, 2023

(30) Foreign Application Priority Data

May 26, 2022 (TW) ................................. 111119674

(51) Int. Cl.
*A61B 17/42* (2006.01)
*A61B 1/32* (2006.01)

(52) U.S. Cl.
CPC ................ *A61B 17/42* (2013.01); *A61B 1/32* (2013.01)

(58) Field of Classification Search
CPC ......... A61B 17/42; A61B 1/32; A61B 1/0684; A61B 17/3439; A61B 1/303; A61B 1/0661; A61B 17/02; A61B 17/0293; A61B 90/30; A61B 17/0206; A61B 2017/0212; A61B 17/0218; A61B 17/3423; A61B 2017/3427; A61B 2017/3425; A61B 2017/3429; A61B 2017/345; A61B 2017/3452; A61B 2017/4216; A61B 2017/4225; A61M 29/00; A61M 2210/1475; A61M 31/00
See application file for complete search history.

(56) References Cited

U.S. PATENT DOCUMENTS

| | | | | |
|---|---|---|---|---|
| 2001/0012950 | A1* | 8/2001 | Nishtala | A61M 25/0662 606/198 |
| 2003/0069476 | A1* | 4/2003 | Deslauriers | A61B 1/32 600/207 |
| 2019/0223708 | A1* | 7/2019 | Recanati | A61B 1/303 |

FOREIGN PATENT DOCUMENTS

| | | | | |
|---|---|---|---|---|
| CN | 106963333 A | * | 7/2017 | .............. A61B 1/06 |
| EP | 0340923 A1 | * | 11/1989 | |

* cited by examiner

*Primary Examiner* — Katherine M Shi
(74) *Attorney, Agent, or Firm* — Muncy, Geissler, Olds & Lowe, P.C.

(57) ABSTRACT

The invention provides a vaginal dilator including a spiral body and a control rod, wherein the spiral body includes a first surface, a second surface, a buckling edge, a fixing seat and a plurality of positioning seats. The buckling edge is adjacent to the first surface and the second surface. The fixing seat is arranged on a side of the first surface which is adjacent to the buckling edge. The plurality of positioning seats are separately arranged on an other side of the first surface opposite to the side provided with the fixing seat. The control rod includes a locking end locked on the fixing seat.

7 Claims, 9 Drawing Sheets

VAGINAL DILATOR

FIELD OF THE INVENTION

The invention relates to an examination tool, and more particularly, to a vaginal dilator for gynecological vaginal examination.

BACKGROUND OF THE INVENTION

Vaginal dilators are the most frequently used tool during gynecological examination processes. Upper and lower dilating sheets, commonly called duckbill dilators, are the most common tools in vaginal examination. However, when such examination tools are used, since the dilating sheets only support upper and lower vaginal walls, there is no protection and blocking function on side vaginal walls. Needle tip devices easily injure the side vaginal wall tissue during the vaginal surgery, and excessive side wall tissues between the upper and lower dilating sheets also cause the doubt of blocking the surgical field of view.

The conventional vaginal examination tools have been improved by increasing the width of the metal sheet and adding the multi-sheet structure. However, the fundamental problems cannot be solved and the difficulty of putting the tool into the vagina may be increased. In addition, other examination tools improved as a balloon type. However, the needle tip device easily damages balloon during the surgery. Therefore, the operations are not ideal. Especially, if there is fluid built up or other conditions during the examination, it may not be removed in time and also indirectly interferes examination on an affected part. Therefore, the inventors focused to study and proposed an easy-to-operate vaginal dilator, so as to overcome the disadvantages of conventional techniques.

SUMMARY OF THE INVENTION

An object of the invention is to provide a vaginal dilator, which is easy to operate, expands field of vision and protects the vaginal wall, thereby improving safety. In addition, auxiliary accessories are selectively arranged according to different examinations or surgeries.

In order to achieve the above object, the invention provides a vaginal dilator including a spiral body and a control rod. The spiral body is formed by a rectangular sheet. The spiral body includes a first surface, a second surface, a buckling edge, a fixing seat and a plurality of positioning seats. The first surface and the second surface are formed along a long axis of the rectangular sheet and are arranged opposite to each other. The buckling edge is formed along a short axis of the rectangular sheet and is adjacent to the first surface and the second surface. The fixing seat is arranged on a side of the first surface which is adjacent to the buckling edge. Each of the plurality of positioning seats is formed along the short axis of the rectangular sheet. The plurality of positioning seats are separately arranged on an other side of the first surface opposite to the side provided with the fixing seat. The control rod includes a locking end and an operating end opposite to the locking end. The locking end is locked on the fixing seat. The control rod is controlled to wind the spiral body into a spiral shape and leads the buckling edge being clamped to one of the plurality of positioning seats.

Further, the buckling edge is arc-shaped.

Further, the plurality of positioning seats are equidistantly arranged on the first surface.

Further, the plurality of positioning seats are L-shaped in cross-section, each of the plurality of positioning seats comprises a first side and a second side connected to the first side, and the first side is connected to the first surface.

Further, each of the plurality of positioning seats is provided with a silicone layer.

Further, the spiral body is assembled with an illumination unit.

Further, the operating end of the control rod comprises an anti-slip layer.

Thus, the invention has the following beneficial effects comparing with conventional technique.

The control rod of the vaginal dilator of the invention is controlled to wind the spiral body into a spiral shape and leads the buckling edge to be clamped to one of the plurality of positioning seats, so that the vaginal dilator expands the vagina by increasing the tube diameter. Thereby, it is convenient to use the control rod to be clamped on the corresponding one of the plurality of positioning seats. It is easy to adjust the size of the tube diameter. It is also convenient to reduce field of view being blocked when observing vagina. It protects vaginal wall from surgical injury. Previously used auxiliary device may be used with the vaginal dilator. The invention increases convenience during examination or surgery.

DETAILED DESCRIPTION OF THE PREFERRED EMBODIMENTS

Several preferred embodiments are presented together with the drawings to illustrate the structural features and operation of the application, which are described below for reference. Referring to FIG. 1, FIG. 2, FIG. 3, FIG. 4, FIG. 5, FIG. 6, FIG. 7A, and FIG. 7B, the invention provides a vaginal dilator 100 including a spiral body 10 and a control rod 20.

Figure 7A:
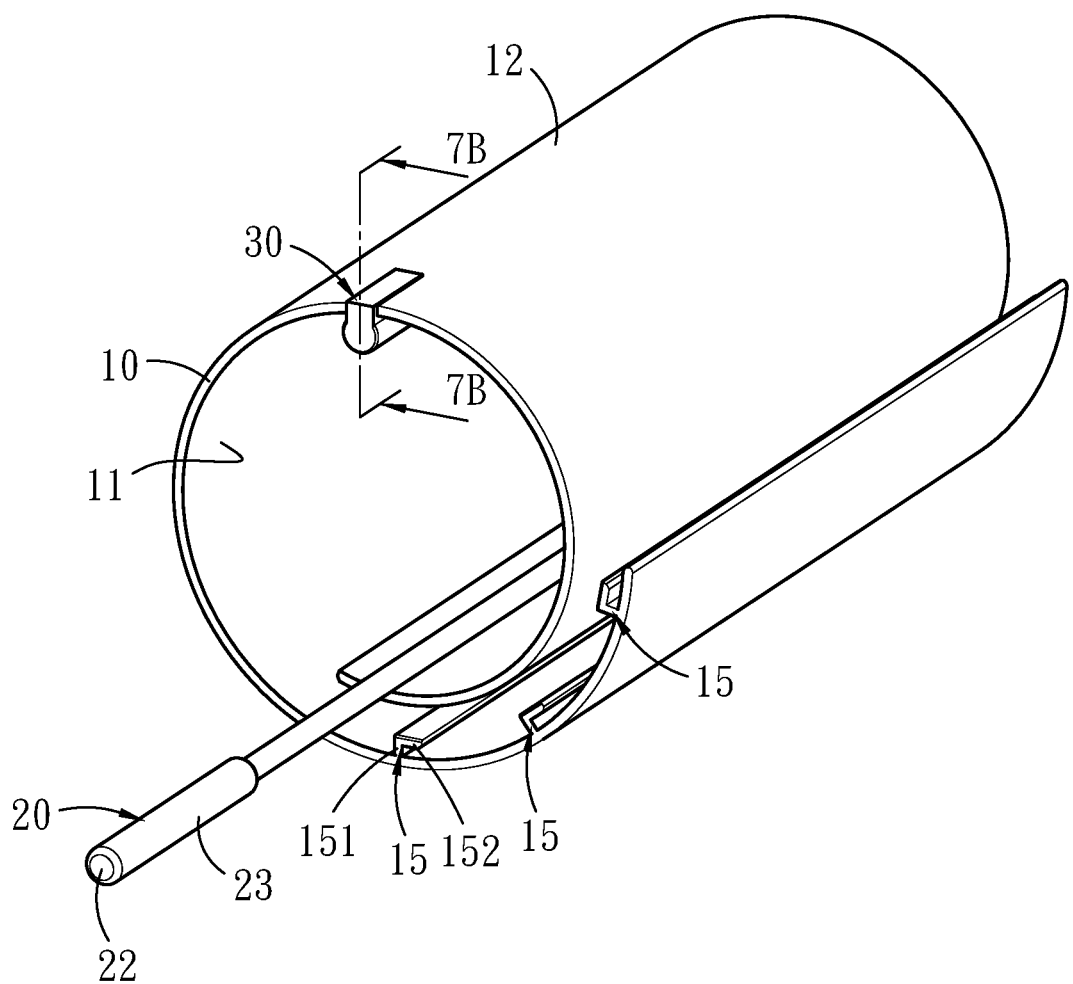
FIG. 7A is a schematic diagram showing an assembled illumination unit of the vaginal dilator of the invention.
Figure 7B:
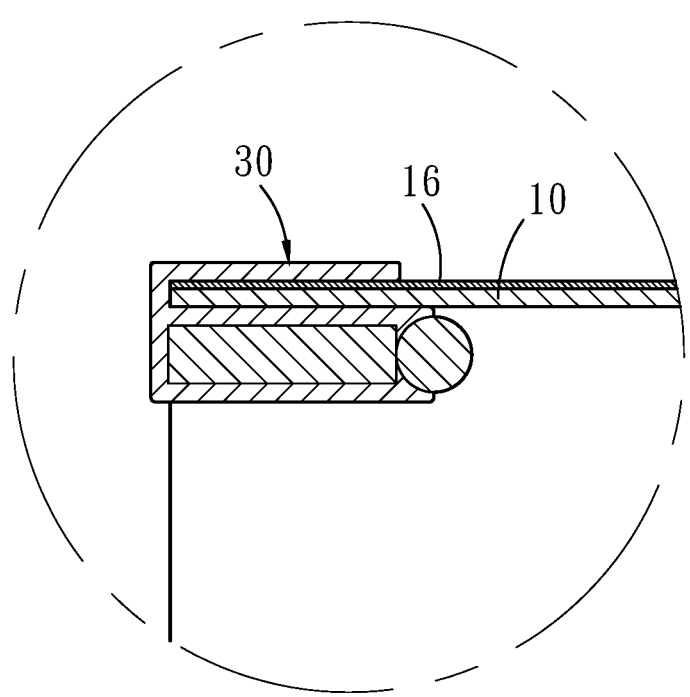
FIG. 7B is a partial section view of FIG. 7A taken along line 7B-7B.

The spiral body 10 is formed by a rectangular sheet body having a long axis and a short axis. The spiral body 10 includes a first surface 11, a second surface 12, a buckling edge 13, a fixing seat 14 and a plurality of positioning seats 15. The first surface 11 and the second surface 12 are formed along the long axis and are arranged opposite to each other. The buckling edge 13 is formed along the short axis and is adjacent to the first surface 11 and the second surface 12. The buckling edge 13 is arc-shaped. The fixing seat 14 is arranged on a side of the first surface 11 which is adjacent to the buckling edge 13. Each of the plurality of positioning seats is formed along the short axis. The plurality of positioning seats 15 are separately arranged on an other side of the first surface 11 opposite to the side provided with the fixing seat 14. The plurality of positioning seat 15 include a first side 151 and a second side 152 connected to the first side 151. The cross sections of the plurality of positioning seats 15 are L-shaped. The first side 151 is connected to the first surface 11. As shown in FIG. 7B, a silicon layer 16 is provided on surface of the spiral body 10. Referring to FIG. 7A, surface of the plurality of positioning seats 15 is also provided with the silicon layer 16 (not shown). The plurality of positioning seats are equidistantly arranged on the first surface 11, but not limited thereto.

Figure 1:
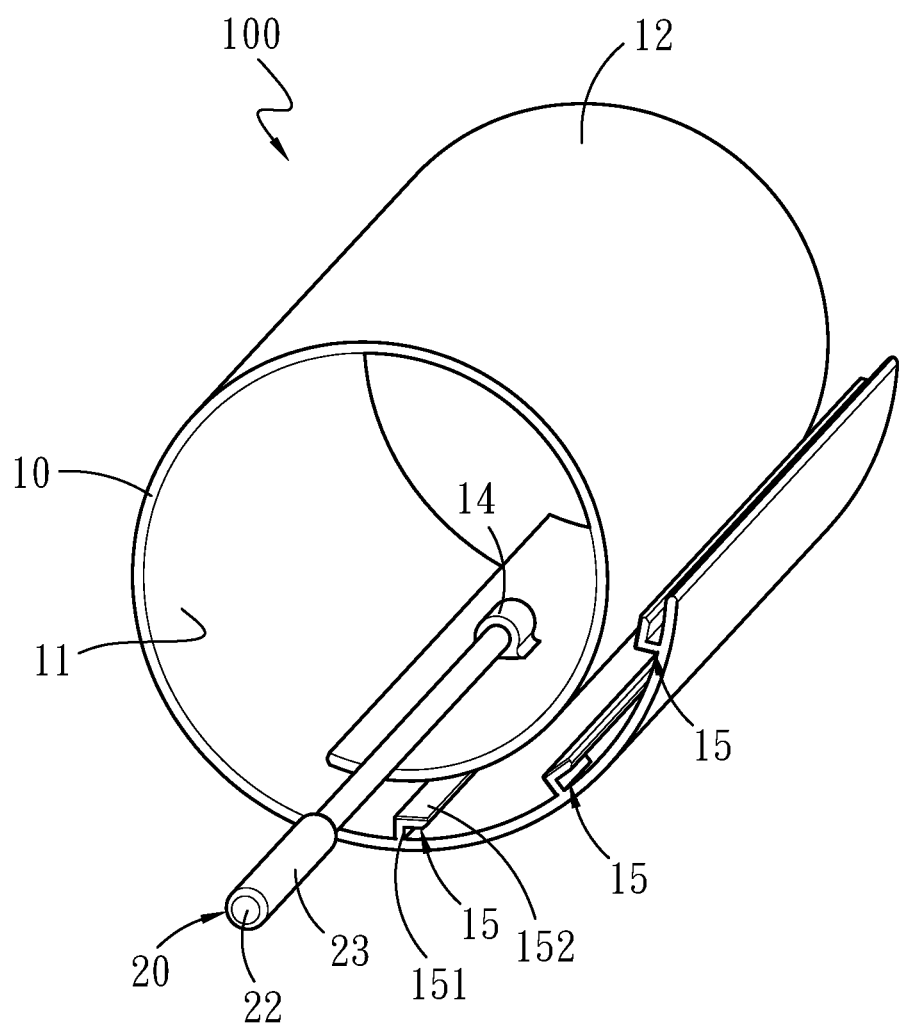
FIG. 1 is a perspective view of a vaginal dilator of the invention.
Figure 2:
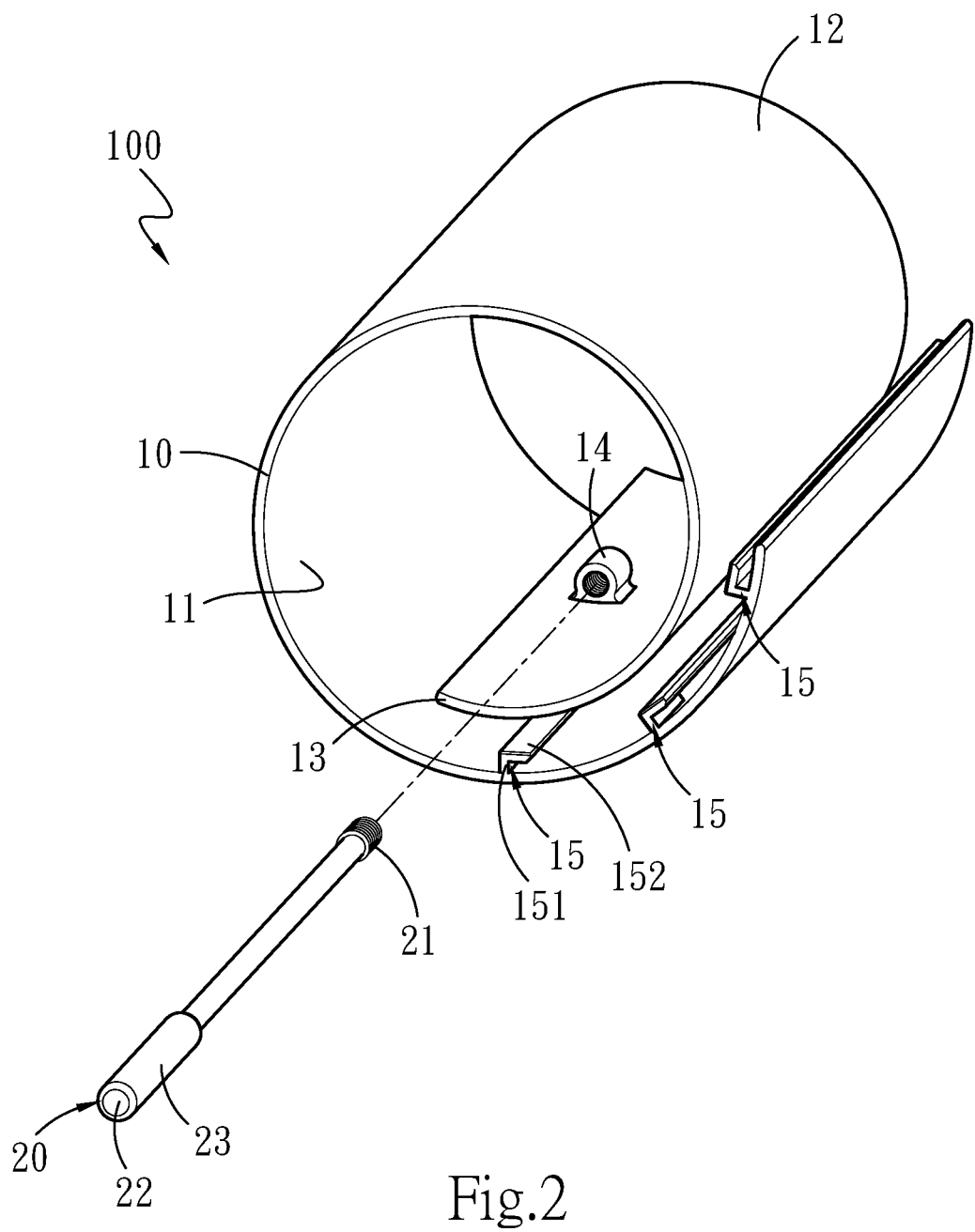
FIG. 2 is an exploded perspective view of the vaginal dilator of the invention.
Figure 3:
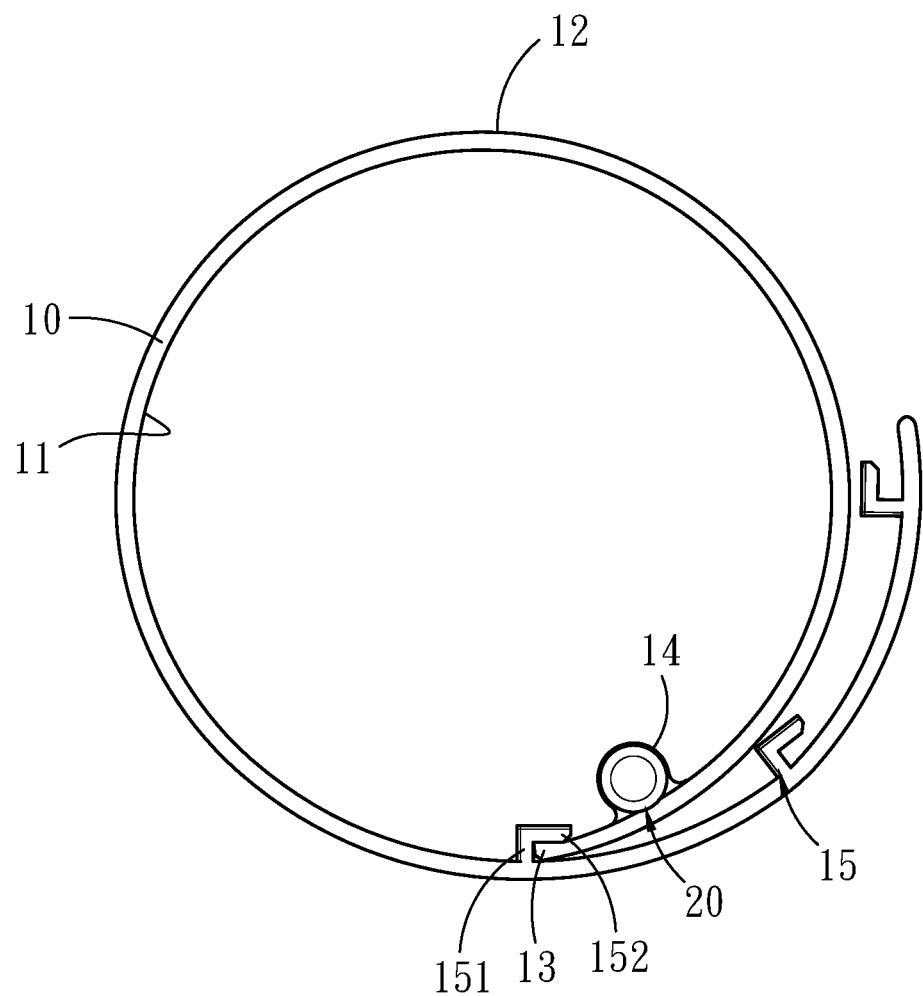
FIG. 3, FIG. 4, FIG. 5, and FIG. 6 are schematic diagrams showing operational states of the vaginal dilator of the invention.

Referring to FIG. 1 and FIG. 2, the control rod 20 includes a locking end 21 and an operating end 22 opposite to the locking end. The locking end 21 is locked on the fixing seat 14. The operating end 22 of the control rod 20 includes an anti-slip layer 23.

The control rod 20 is controlled to wind the spiral body 10 into a spiral shape. The control rod 20 leads the buckling edge 13 being clamped to one of the plurality of positioning seats 15 to adjust a tube diameter of the spiral body 10. Referring to FIG. 7A, an illumination unit 30 is provided on the spiral body 10 by a medical staff according to requirements. The illumination unit 30 provides light from the first surface 11.

Figure 4:
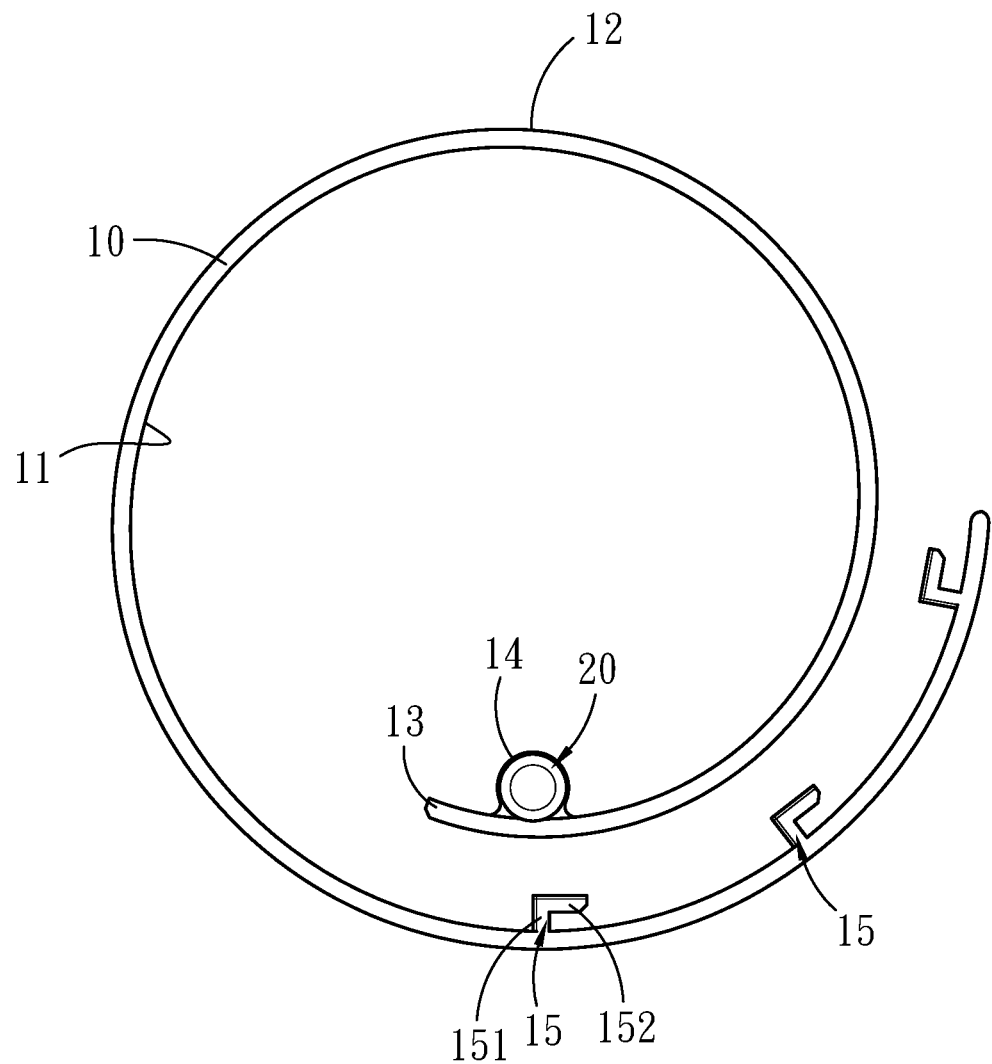
Figure 5:
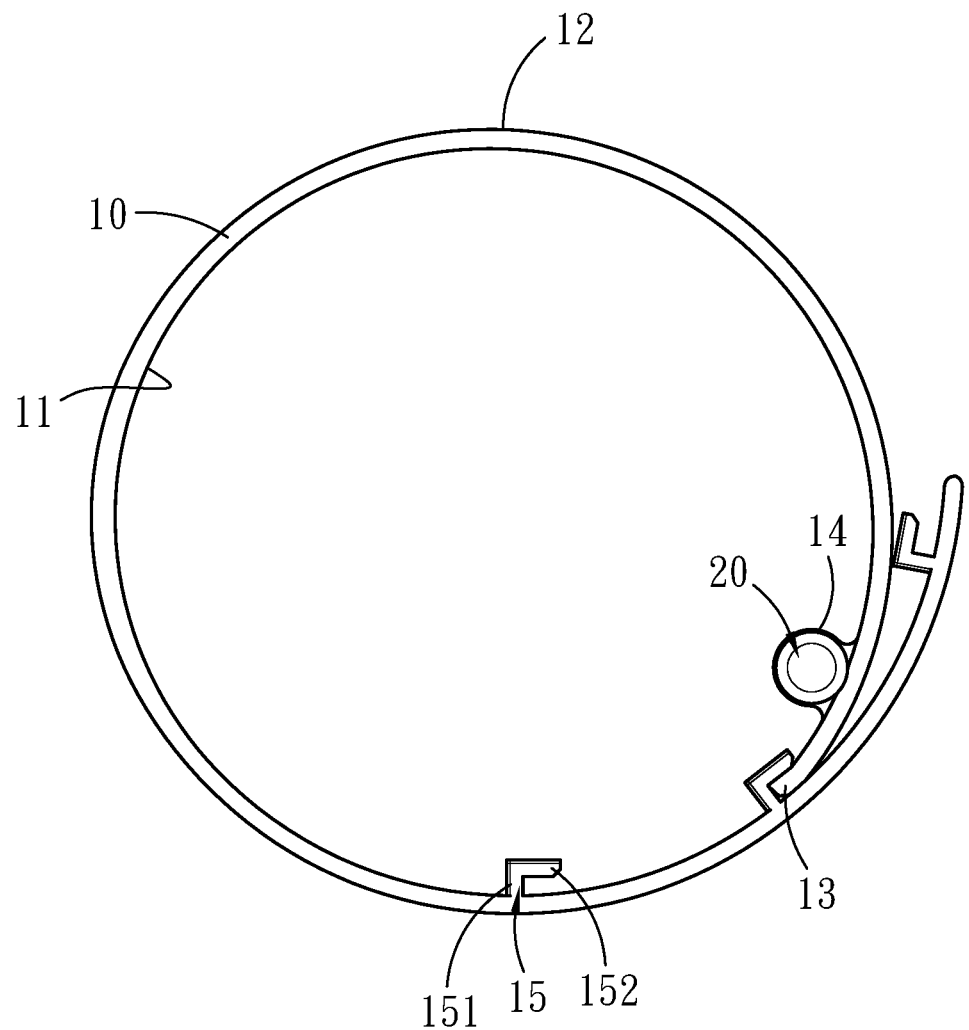
Figure 6:
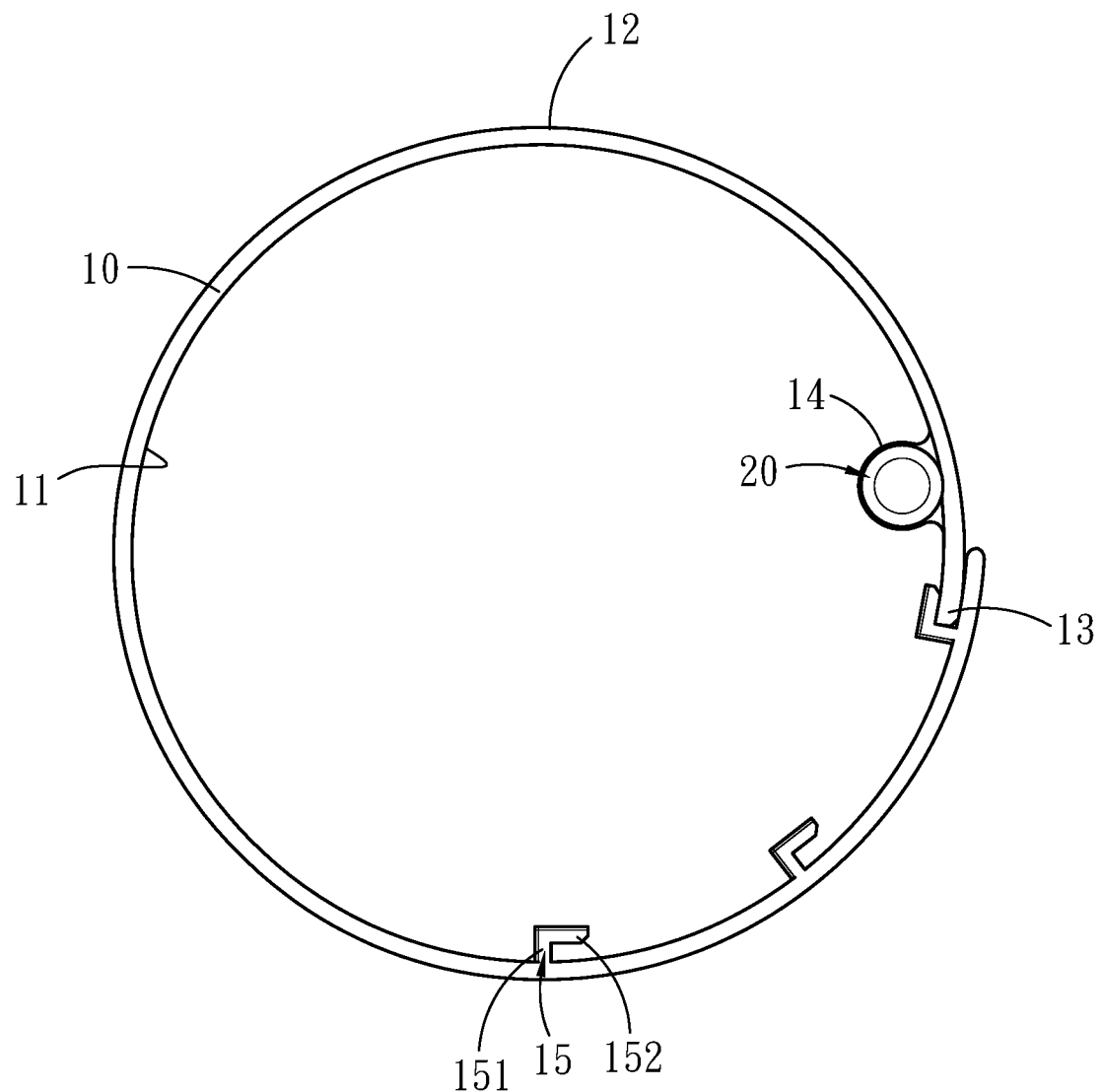

Referring to FIG. 3, FIG. 4, FIG. 5, and FIG. 6, when the medical staff places the vaginal dilator 100 on vaginal wall of a patient, if the tube diameter of the vaginal dilator 100 needs to be adjusted to be larger, referring to FIG. 4, the medical staff uses the control rod to control the buckling edge 13 of the spiral body 10 to be removed from the plurality of positioning seat 15 which is originally locked and fixed. Referring to FIG. 5 and FIG. 6, the medical staff needs to lock and fix the buckling edge 13 at an other one of plurality of positioning seat 15 corresponding to the desired tube diameter. Furthermore, if light is insufficient, as shown in FIG. 7A and FIG. 7B, the medical staff may fix the illumination unit 30 on the spiral body 10 and enable the illumination unit 30 to provide the required illumination brightness from the first surface 11 of the spiral body 10. It can be seen from FIG. 7B that the spiral body 10 is provided with the silicone layer 16 including a protective function.

Figure 8:
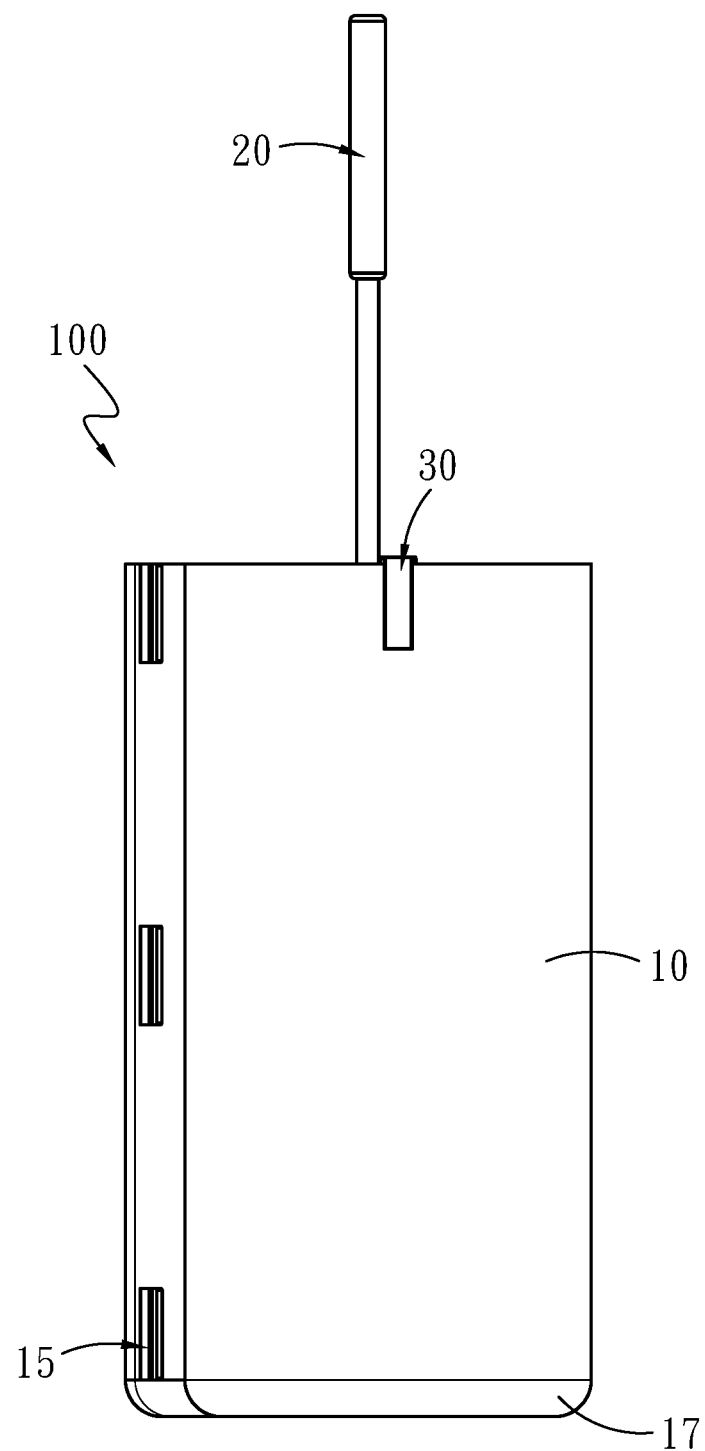
FIG. 8 is a side view of a vaginal dilator of another embodiment of the invention.

Further, referring to FIG. 8, which is another embodiment of the vaginal dilator 100 of the invention, the main structure and function of the vaginal dilator 100 are substantially the same as those of the vaginal dilator 100 described above, and are not described in details. The main difference is that the spiral body 10 is formed with a fillet edge 17 along the long axis. The fillet edge 17 is inserted to end of the vaginal wall. The fillet edge 17 allows the vaginal dilator 100 to be inserted without unnecessary damage to the vaginal wall such as scratching.

In view of the above, the control rod 20 of the vaginal dilator 100 of the invention winds the spiral body 10 into a spiral shape and leads the buckling edge 13 to be clamped to one of the plurality of positioning seats 15 according to a desired tube diameter, so that the vaginal dilator 100 expands the vagina by increasing the tube diameter. Thus, it allows the vaginal dilator 100 to be easily locked and clamped to the corresponding one of the plurality of positioning seats 15 through the control rod 20, thereby easily adjusting the tube diameter of the vaginal dilator 100 and also reduces field of view being blocked when observing vagina. It protects vaginal wall from surgical injury, and common auxiliary devices can be used in combination with the vaginal dilator 100, so as to increase the convenience during examination or surgical operation.

What is claimed is:

1. A vaginal dilator, comprising:
   a spiral body, formed by a rectangular sheet, and the spiral body comprising a first surface, a second surface, a buckling edge, a fixing seat and a plurality of positioning seats, wherein the first surface and the second surface are formed along a long axis of the rectangular sheet and are arranged opposite to each other, the buckling edge is formed along a short axis of the rectangular sheet and is adjacent to the first surface and the second surface, the fixing seat is arranged on a side of the first surface which is adjacent to the buckling edge, each of the plurality of positioning seats is formed along the short axis of the rectangular sheet, and the plurality of positioning seats are separately arranged on an other side of the first surface opposite to the side provided with the fixing seat; and
   a control rod, comprising a locking end and an operating end opposite to the locking end, wherein the locking end is locked on the fixing seat;
   wherein the control rod is controlled to wind the spiral body into a spiral shape and leads the buckling edge being clamped to one of the plurality of positioning seats.

2. The vaginal dilator according to claim 1, wherein the buckling edge is arc-shaped.

3. The vaginal dilator according to claim 1, wherein the plurality of positioning seats are equidistantly arranged on the first surface.

4. The vaginal dilator according to claim 1, wherein the plurality of positioning seats are L-shaped in cross-section, each of the plurality of positioning seats comprises a first side and a second side connected to the first side, and the first side is connected to the first surface.

5. The vaginal dilator according to claim 1, wherein surface of the spiral body is provided with a silicone layer.

6. The vaginal dilator according to claim 1, wherein the spiral body is assembled with an illumination unit.

7. The vaginal dilator according to claim 1, wherein the operating end of the control rod comprises an anti-slip layer.

* * * * *